United States Patent [19]

Newborough et al.

[11] Patent Number: 5,193,740
[45] Date of Patent: Mar. 16, 1993

[54] DISPOSABLE FOLD-UP CONTAINER FOR USED MEDICAL MATERIALS

[75] Inventors: Mark Newborough, Westhouses; Neil B. Whatmough, Oldham, both of United Kingdom

[73] Assignee: Cundell Decorprint Limited, United Kingdom

[21] Appl. No.: 865,698

[22] Filed: Apr. 8, 1992

[30] Foreign Application Priority Data

Feb. 12, 1988 [GB] United Kingdom ............... 8803288
May 25, 1988 [GB] United Kingdom ............... 8812371

[51] Int. Cl.$^5$ ............................................. B65D 5/00
[52] U.S. Cl. ............................. 229/3.5 MF; 229/200; 229/242; 206/366; 206/370; 220/405; 220/450; 110/241
[58] Field of Search .............. 206/365, 366, 370; 220/405, 419, 450, 908; 229/200, 222, 242, 3.5 MF, DIG. 2; 383/113; 110/241

[56] References Cited

U.S. PATENT DOCUMENTS

| | | | |
|---|---|---|---|
| 643,593 | 2/1900 | Cox ................................ | 110/241 |
| 1,147,189 | 7/1915 | Rue ................................ | 110/241 |
| 2,106,499 | 1/1938 | Francisco .................. | 229/3.5 MF |
| 2,310,712 | 2/1943 | Schmied ..................... | 229/3.5 MF |
| 2,322,345 | 6/1943 | Cage ............................ | 229/3.5 MF |
| 2,830,001 | 4/1958 | Barnes et al. .............. | 229/3.5 MF |
| 3,341,102 | 9/1967 | Stephens et al. ........... | 229/3.5 MF |
| 3,498,240 | 3/1970 | Trott ............................ | 110/241 |
| 3,829,006 | 8/1974 | Spiegel ......................... | 229/242 |
| 4,158,412 | 6/1979 | Wysocki ...................... | 229/242 |
| 4,240,363 | 12/1980 | Troy ............................. | 383/113 |
| 4,452,358 | 6/1984 | Simpson ...................... | 206/366 |
| 4,863,052 | 9/1989 | Lambert ...................... | 206/366 |
| 5,057,656 | 10/1991 | Galber ......................... | 206/366 |
| 5,065,939 | 11/1991 | Boothe et al. .............. | 206/366 |

FOREIGN PATENT DOCUMENTS

| | | |
|---|---|---|
| 237418 | 2/1960 | Australia . |
| 251237 | 9/1962 | Australia . |
| 264032 | 2/1964 | Australia . |
| 269616 | 4/1964 | Australia . |
| 255562 | 5/1965 | Australia . |

*Primary Examiner*—David T. Fidei
*Attorney, Agent, or Firm*—D. Peter Hochberg; Mark Kusner

[57] ABSTRACT

A fold-up container for holding and incinerating disposable syringes is comprised of a base panel, a top panel, and a plurality of side panels hingeably connected to one another along a plurality of fold lines to define a closed container having an internal chamber dimensioned to receive one or more disposable syringes. An access opening into the chamber is formed by a peripheral weakened line defining a tear strip, the weakened line being located in at least one of the side panels and extending into a portion of the top panel. The carton is formed of a corrugated paper-based fluting having an inner metal foil layer secured to one side of the fluting and outer paper-based layer secured to the opposite side fluting. The container resists puncturing by a syringe and maintains sufficient structural integrity to facilitate destruction of syringes by internal burning before the container itself is destroyed by burning.

4 Claims, 6 Drawing Sheets

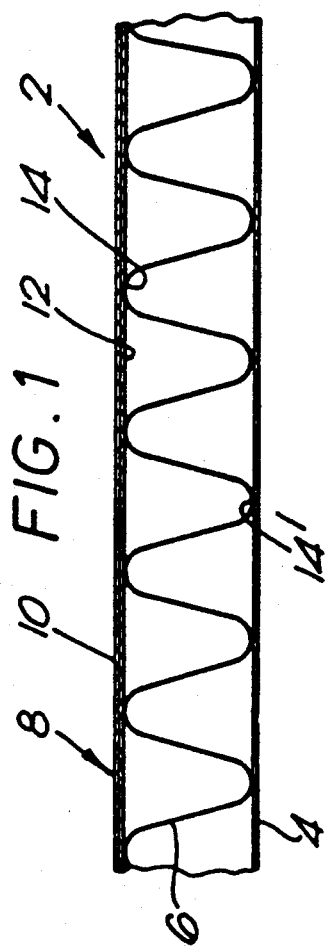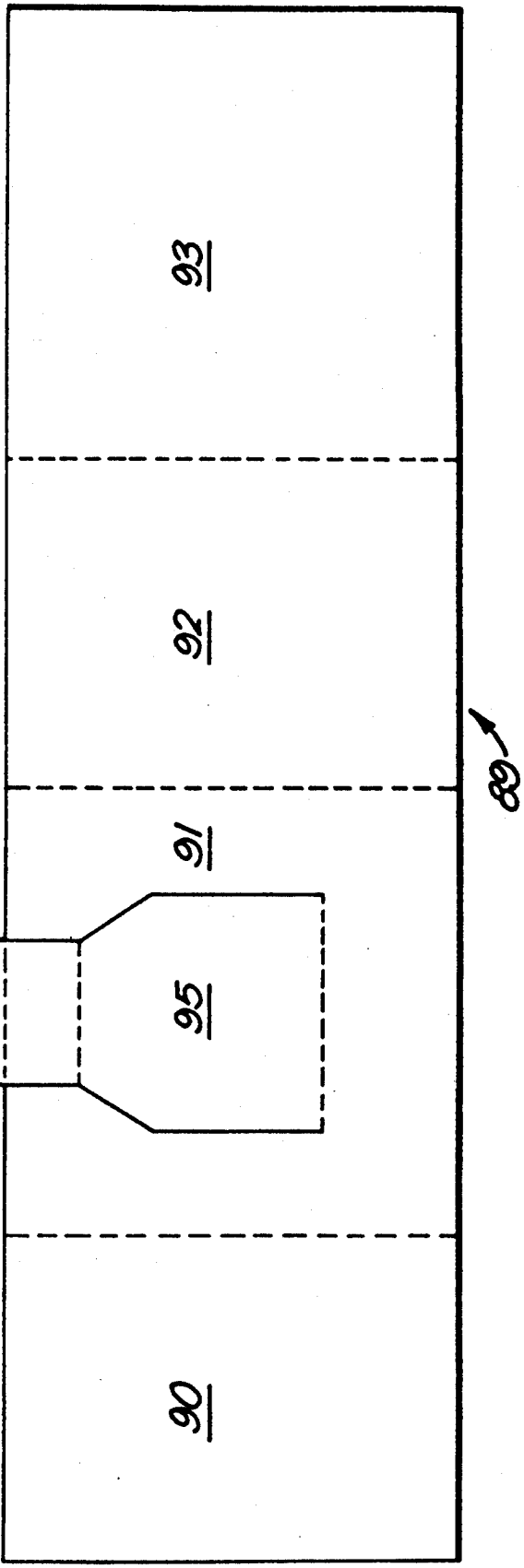

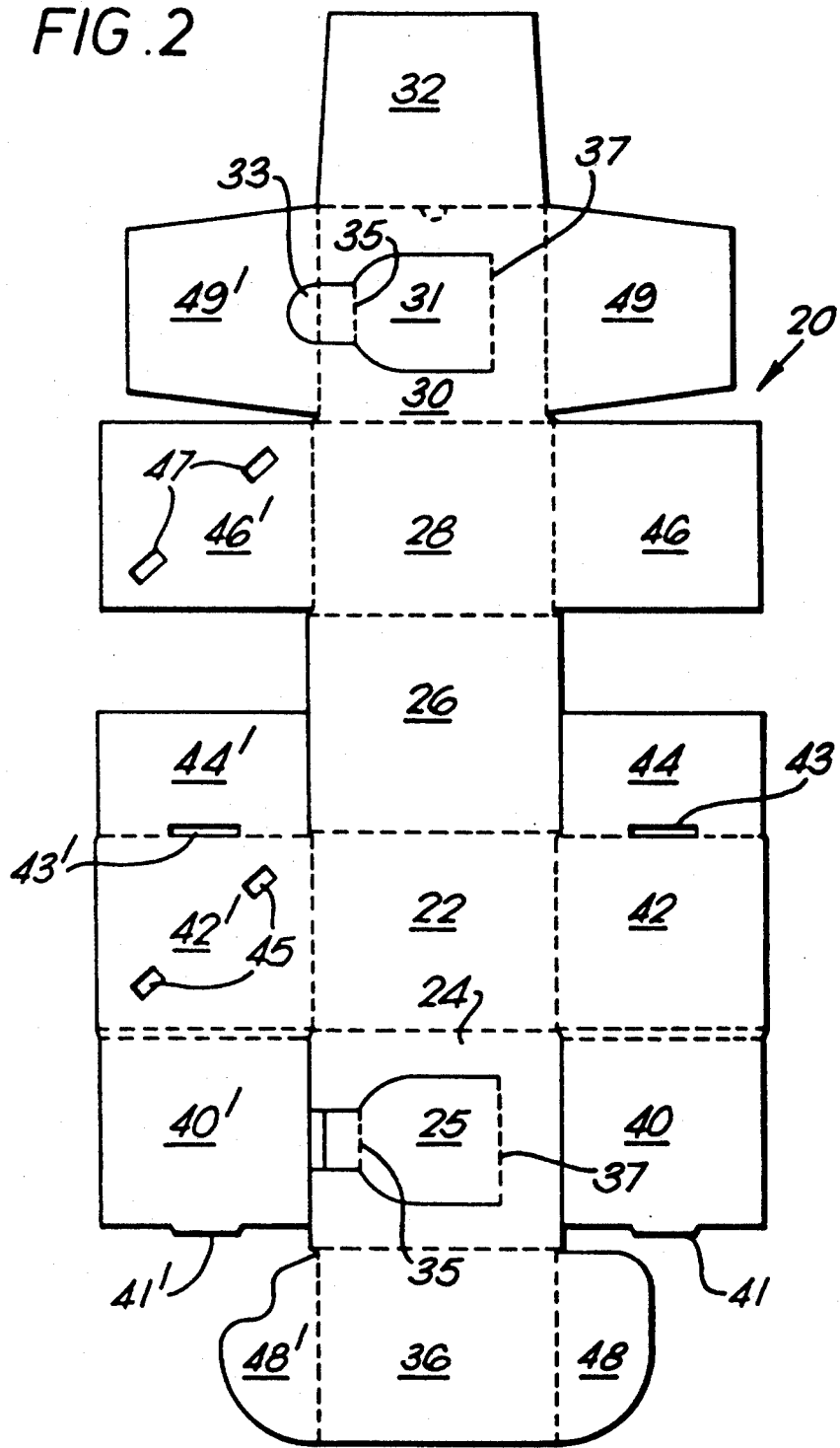

DISPOSABLE FOLD-UP CONTAINER FOR USED MEDICAL MATERIALS

This is a continuation of co-pending application Ser. No. 07/555,417 filed on Oct. 9, 1990, now abandoned.

FIELD OF THE INVENTION

This invention relates to a container and is more particularly concerned with a container in which disposable articles, such as plastic syringes and their associated metal needles, may be placed and then incinerated.

BACKGROUND OF THE INVENTION

There is a need, particularly in third-world countries in which mass-inoculation programmes are being carried out, for a cheap, simple container which can be used for collecting spent syringes and needles and, subsequently, for disposing by burning of the collected articles by igniting the articles within the container. Such a container must be sufficiently robust to resist puncturing by the needles collected and must be capable of maintaining its structural integrity for a prolonged period whilst the contents are being burnt. If the material from which the container is made is consumed too quickly by the burning contents, there is a danger that a small proportion of the articles being disposed of may escape destruction and may eventually come to be used a second time. This problem is of particular concern as it may lead to the transmission of contagious diseases via a contaminated syringe/needle.

SUMMARY OF THE INVENTION

According to the present invention, there is provided a closed container made from at least one blank of foldable material for the incineration of disposable articles, the container being provided with means permitting access to the interior of the container for insertion of said disposable articles into the container, and substantially the whole of the inner surface of the container being constituted by a relatively thin metallic layer.

Preferably, the foldable material from which the container is constructed is a corrugated material comprising a fluted material to which is laminated, on solution to the provision of a further thickness of material in the walls of the container.

Both the single blank and double blank embodiments of the container of the present invention may include weakened regions which constitute the means permitting access to the interior of the container. Thus, in a wall of the container having, for example, a double thickness, overlapping weakened regions may be provided, the inner of the overlapping regions having a tab which projects through the outer region and enables the two weakened regions to be pulled out together and folded back to reveal an aperture communicating with the interior of the container. In preferred embodiments, the weakened regions may be creased in such a manner that two distinct open positions can be attained depending upon the force applied to the tab. Thus, a first open position where only part of the weakened region is broken will reveal a relatively small aperture for disposal of syringes. This small aperture may be enlarged by applying a further pulling force to the tab to break the remaining weakened portions and to reveal a larger aperture through which a firelighter may be introduced into the container for incinerating purposes.

The aperture to the container should be of a size sufficient to permit insertion of the articles to be disposed of and insertion of a firelighter to cause ignition of the contents of the container. However, the aperture should not be so large as to enable manual removal of the contents of the container. However, the aperture should not be so large as to enable manual removal of the contents of the container. The aperture may be of any shape; for example, the aperture may be circular with a diameter just large enough to permit insertion into the container of a circular cross-section syringe. Alternatively, a rectangular aperture may optionally be employed. Preferably, the maximum width of the aperture is 50 mm, more preferably one side, a first liner and, on the other side, a metal foil layer. One presently preferred material comprises a first paper-based liner which is spaced from the metal foil layer by corrugated paper-based fluting, the first sheet and the metal foil layer being secured to the flute tips, for example by means of an adhesive. Most preferably, the metal foil is an aluminium or ferric foil. However, any metal or alloy capable of being formed in thin layers but which is not easily combustible is suitable. In preferred embodiments, the metal foil is secured or laminated to a paper layer which paper layer is then secured to the flute tips. The corrugated paper-based material may be replaced by, for instance, a corrugated plastic having a high melting point.

The container of the present invention may be made from a single blank of foldable material, the foldable material being provided, on one side thereof, with the metal foil layer. Preferably, the blank is made from the corrugated material described above. When the blank is folded and the container assembled, the foil layer is to the inside of the container. With certain designs of blanks, it is possible that a small amount of a cardboard or paper surface will be exposed on the inside of the container. This does not pose a problem so long as the exposed cardboard or paper does not cover too large an expanse of the container's inner surface.

The corrugated material described above is particularly advantageous as it gives, in use, an insulating effect and prolongs the duration of incineration for which the container itself remains unburnt. This insulating effect combines with the heat-resistant effects of the metal layer to provide a particularly useful container for incinerating disposable articles.

It has been found that a container in accordance with the present invention retains its structural integrity for longer periods if the sides of the container comprise several layers. This has also been found to reduce the changes of a needle piercing the entire skin of the container, which could give a risk of contamination to a user. It has been found that advantageous results are achieved when opposite end walls of the container are at least four layers thick. Preferably, the remaining four walls are at least two layers thick. The thickness of the end walls is more critical as the disposable syringes and needles tend to lie along the major axis of the container between the end walls.

The container may be provided with a carrying handle for ease of transport.

In one embodiment of the present invention, the container is made from a single blank of foldable material which, when folded, yields a container having walls and sides of the desired multiple thickness and also other features such as the carrying handle.

Alternatively, the container may be made from two separate blanks of foldable material, one of which constitutes an outer shell when folded, the other of which constitutes, when folded, an inner lining of the container. By using two such blanks, the container may be more economically produced and, in addition may be designed as a carrying pack for unused syringes. Such a pack can be opened at its destination for dispensing the new, unused syringes and maybe closed again so as to form an incinerating container. This carrying facility is not as straightforward where the container is made from a single blank as removal of syringes in the interior of the container may require complete disassembly of the container rather than simple opening of one end. The inner lining provides a simple 25 mm. The container may be provided with a flap, either on the inside or the outside of the container, to close the aperture when not in use. As is mentioned above, the blank from which the container is assembled may be formed with weakened regions which enable a first small aperture to be formed by breaking certain of the weakened regions and subsequently a larger aperture to be formed by breaking the remaining weakened regions.

The means permitting access to the interior of the container may be in any wall of the container but preferably is in one of the sides other than the end walls, or in the top of the container.

BRIEF DESCRIPTION OF THE DRAWINGS

For a better understanding of the present invention, and to show how it may be carried into effect, reference will now be made, by way of example, to the accompanying drawings, in which:

FIG. 1 shows a section through a corrugated material from which the container of the present invention may be fabricated;

FIG. 2 shows a blank;

FIG. 3 and 4 show two cooperating blanks;

DESCRIPTION OF PREFERRED EMBODIMENTS

Figure 3:
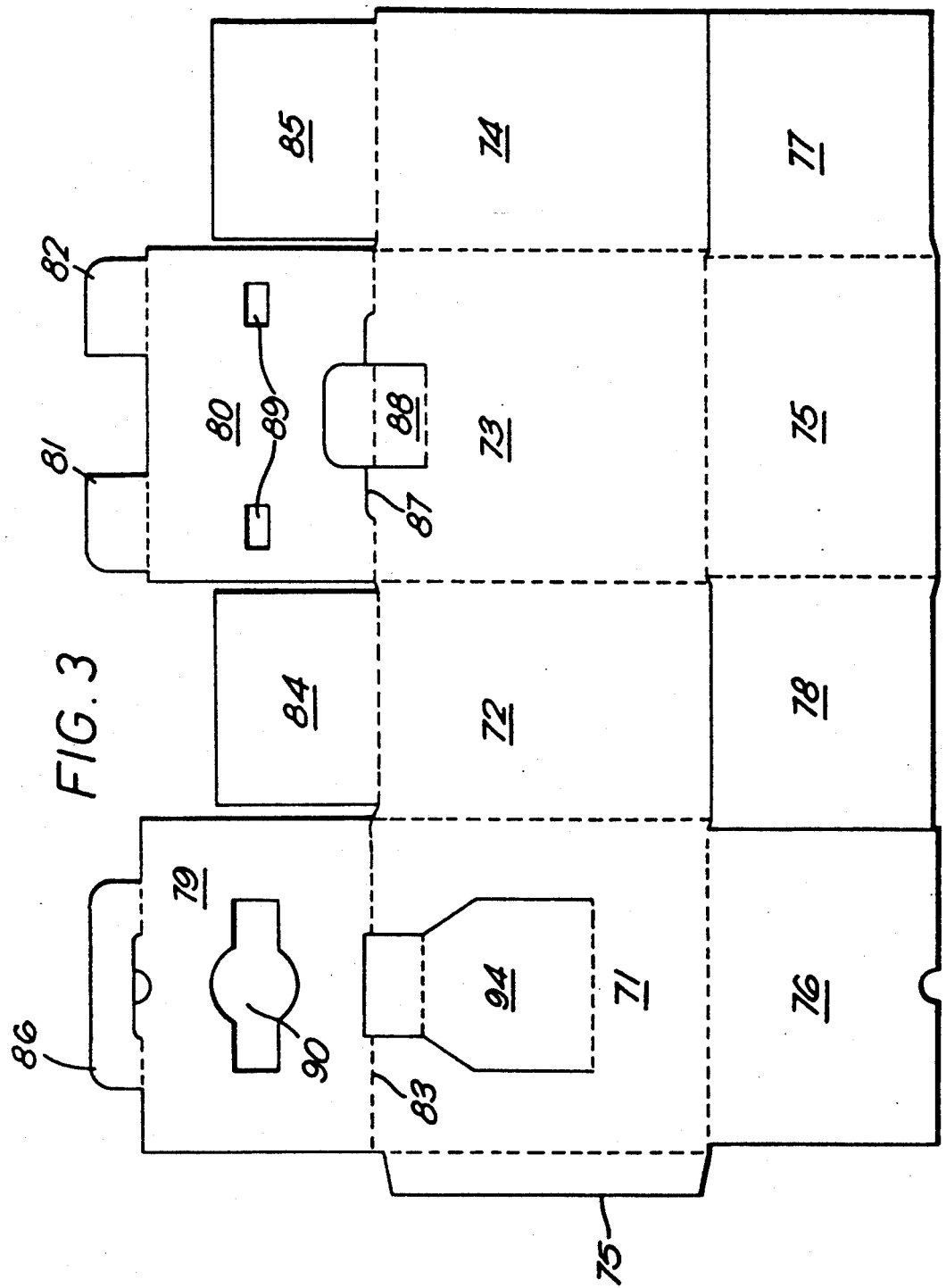

In the Figures, solid lines represent cut edges of a blank, whilst broken lines represent crease lines about which a blank is folded.

Moreover, in all the cartons, the blank is folded such that the foil layer is innermost.

A laminated corrugated cardboard material 1 as shown in FIG. 1 may be used to fabricate a container in accordance with this invention. The material 2 comprises a first, paper-based liner 4, a second, intermediate layer 6 of a fluted material (again paper based) and a third metallized liner 8 which comprises a metal foil 10, for instance aluminium, laminated to kraft paper 12. The liners 4, 8 are secured to the flute tips 14, 14' by an adhesive. In manufacturing this material 1, it is normal first to secure the metallized liner 8 to the flute tips 14 on one side of fluted material 6 and then to secure the first paper-based liner 4 to the flute tips 14' on the other side of the fluted material 6. The first liner 4 may be, for instance, a sheet which is printed, for example, with appropriate instructions for using the container.

The blank 20 shown in FIG. 2 may be made from a single sheet of the material 1 depicted in FIG. 1. When folded, the blank 20 assumes the shape of a box 50 such as that shown in FIG. 5. In describing the blank 20 shown in FIG. 2, reference will be made to the box 50 shown in FIG. 5. Thus, the box 50 has two opposed end walls 52 and 54, a front wall 56, a rear wall 58, a bottom wall 60 and a top wall 62. The front wall 56 is provided with means 25 whereby access to the interior of the container is possible (see below). Although not shown in FIG. 5, the walls of the box 50 may be multi-layered. Thus, if the box 50 is made from the blank 20 shown in FIG. 2 the opposed end walls 52, 54 have four discrete layers, three of the remaining four walls each having two discrete layers. If the box 50 is made from the blanks shown in FIGS. 3 and 4, the end walls 52 and 54 have a quadruple thickness and the remaining walls a double thickness. This "multi-layered" feature of the box 50 is a direct result of the construction and design of the blank or blanks from which the box 50 is created. Thus, referring again to FIG. 2, the blank is shown to comprise a first base panel 22, first front and rear side wall panels 24, 26 and a first top panel 28. In addition, the blank comprises a second front wall panel 30, a second base panel 32 and a second top panel 36. These panels are serially connected by fold lines in the panel order 36-24-22-26-28-30-32 and, in the folded box 50, assemble to give each of the front wall 56, top wall 62 and bottom wall 10 a double thickness. When the serially connected panels are folded as described, panels 36, 24, 22 and 26 are on the outside of the box 50, whilst panels 28, 30 and 32 are on the inside of the box 50.

It should also be noted that, when the blank 20 shown is made of the material shown in FIG. 1, it should be folded in order that the metal layer 8 faces the inside of the box 50.

Moreover, the blank comprises end panels 40, 42 and 44, and 40', 42' and 44' which stand up, when folded, perpendicular to the first base panel 22 to provide the end panels 52 and 54 of the box 50. Panels 40 (40') and 44(44') fold about the fold lines shown to overlay the panel 42 (42'), a projection 41 (41') on panel 40 (40') being accommodated in a slot 43 (43') in panel 44(44') to provide a treble thickness and to create a folded pocket. The folded pockets created by end panels 40, 42 and 44 (40', 42' and 44') stand up at right angles to the first base panel 22. Into each of the pockets is accommodated a flap 46 (46') which projects down, at right angles (when folded) from the first top panel 28 during assembly. This secures together the top and bottom of the box 50 at the same time providing the quadruple thickness of the end walls 52 and 54.

Finally, flaps 48, 48' fold down from the second top panel 36 and are received between panels 42 and 46, and panels 42' and 46' respectively; flaps 49, 49' fold in from the second front wall panel and are received inside the container adjacent the panel 44, 44' respectively.

Each of the first and second front wall panels 24 and 30 are provided with weakened areas 25 and 31 respectively shown by unbroken lines. These weakened areas 25,31 are capable of being pushed open to yield an aperture. In the closed container, the weakened areas 25 and 31 overlap and a tab 33 projects from the weakened area of the inner front wall panel 30 through the outer front wall panel. This tab 33 may be gripped and pulled to break the weakened regions in two stages; a first stage in which a small aperture is revealed, the weakened regions 25 and 31 folding up to the first crease line 35 and a second stage in which the weakened regions 25 and 31 fold back about the second crease line 37. Folding back to the first crease line 35 reveals a small aperture through which a syringe may be "posted" whilst folding back to the second crease line reveals a larger aperture through which a firelighter may be "posted".

In the embodiment shown in FIG. 2, flap 46' and end panel 42' which overlap in the folded container have holes 45 and 47 through which a strap or handle (not shown) may be passed for carrying the container.

Certain of the panels may, if desired, be secured to other of the panels with, for example, an adhesive.

FIGS. 3 and 4 show the blanks which may be formed into the outer and inner parts respectively of a two part box in accordance with the invention. The outer blank shown in FIG. 3, comprises four serially connected side wall panels 71, 72, 73 and 74 which fold together to form a tube of square cross section. A tab 75 on the end of panel 71 is glued to the outer edge of panel 74 to secure the tube. The base of the outer part is formed by overlying panels 75 and 76; flaps 77 and 78 which append from panel 75 fold back into the container against panels 72 and 74 to provide a secure hold to the base panels 75 and 76.

Top panels 79 and 80 fold together to form the top of the box, panel 77 lying outermost. Tabs 81 and 82 on top of 80 are secured to the inside of the panel 71 at its top edge 83. Flaps 84 and 85 connected to panels 72 and 74 respectively tuck into the box and lie underneath the top of the outer part of the box. An arrangement of (i) a flap 86 connected to panel 70 and (ii) the slot 87 formed at the junction at right angles cooperate in the folded box with the flap 86 projecting onto the slot 87. A tab 88 which can fold back upon itself is used to lock flap 86 into the slot 87.

Through holes 89 a strap may be looped which will project through an aperture 89 in the top panel 79 for easy carrying of the container.

Figure 5:
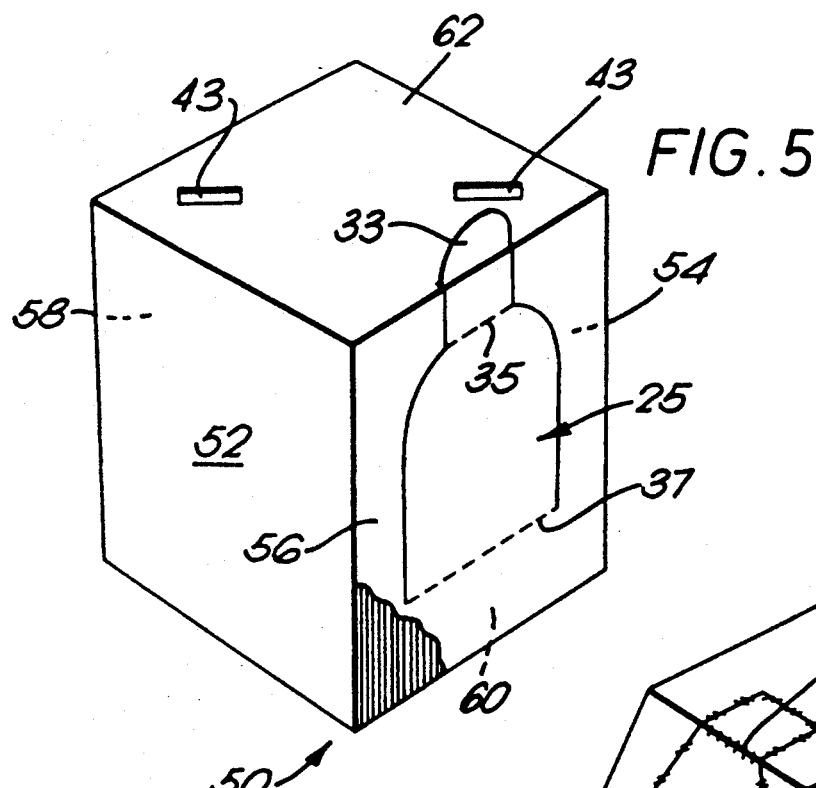
FIG. 5 shows a container erectable from the blank of FIG. 2 or the blanks of FIGS. 3 and 4.

The inner blank comprising serially connected panels 91, 92, 93, 90 shown in FIG. 5 folds into a tubular part of square cross section which is inserted into the open erected outer part such that the panels 90, 91, 92 and 93 lie directly against panels 71, 72, 73 and 74 of the outer part respectively.

Means to permit access to the container is provided in the form of weakened regions 94 (FIG. 3) and 95 (FIG. 4) which overlap to form a similar structure to that described in relation to FIG. 2. A tab 96 projects out through the outer part to enable the weakened regions to be broken thereby enabling access to the interior of the box.

As will be appreciated, the foil layer shields the cardboard material from the heat generated by the burning contents of the container. Tests have shown that containers fabricated using the corrugated material described above retain their structural integrity for up to twenty minutes following ignition of the contents of the container. This means that contaminated contents continue to be retained until fully sterilised and therefore pose no risk of further contamination. Moreover plastic syringes are normally completely destroyed and any residual material in a syringe or needle is also destroyed.

Figure 7:
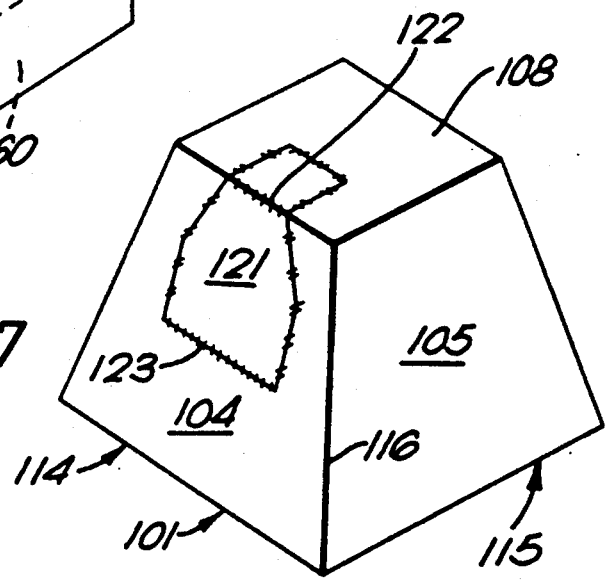
FIG. 7 shows the container erectable from the blank shown in FIG. 7.
Figure 6:
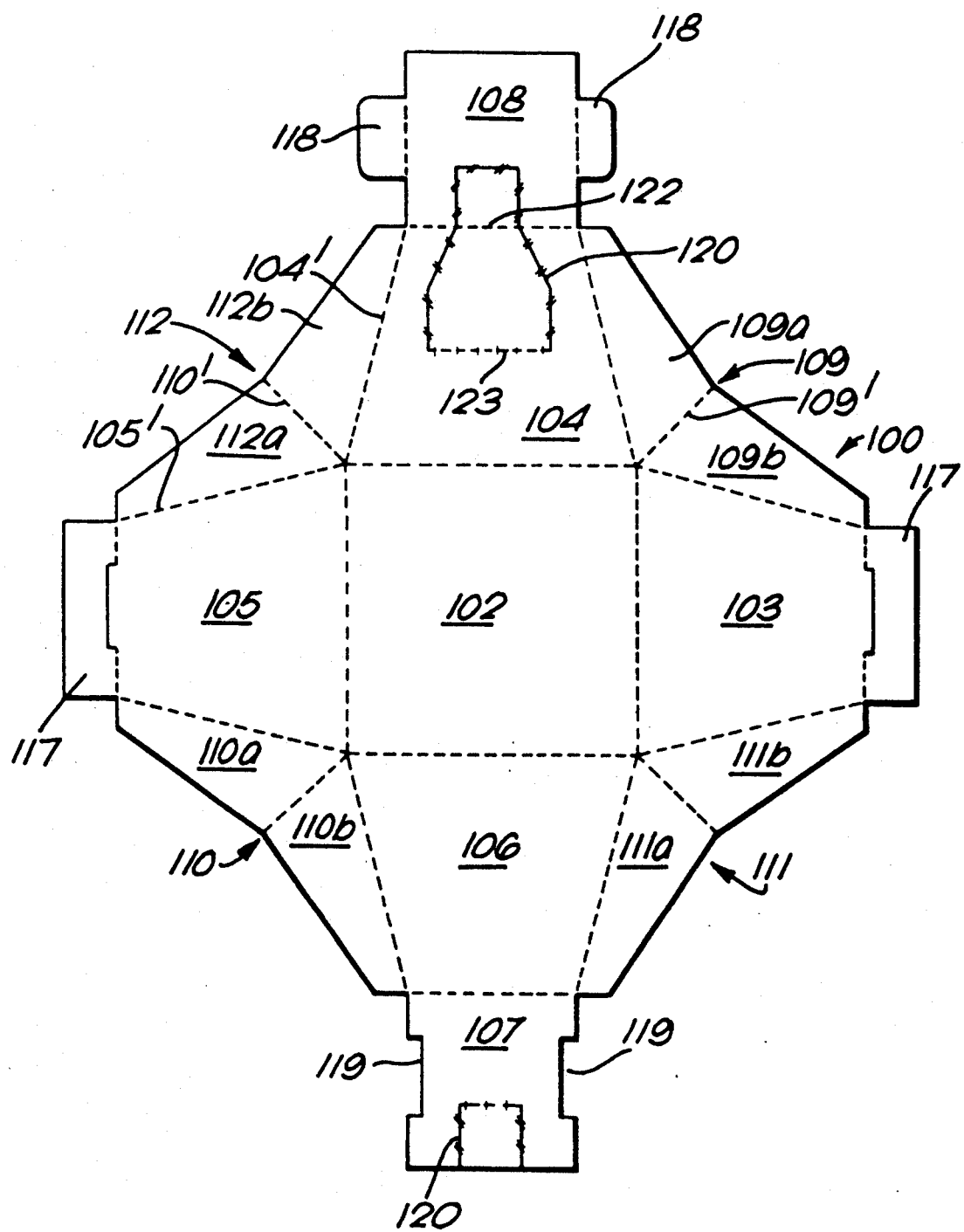
FIG. 6 shows another blank.

FIG. 6 illustrates another blank configuration 100. The blank is made of the material shown in FIG. 1 and should be folded in order that the metal layer faces the inside of the box formed (see FIG. 7). The blank 100 shown in FIG. 6 is erectable into a truncated pyramidal container or box 101 as shown in FIG. 7. The integral blank 100 comprises a square base panel 102 from each side of which there projects a side panel, namely side panels 103, 104, 105 and 106. In addition, blank 100 comprises first and second top panels 107 and 108 separately secured to opposing side panels 106 and 104. In between each adjacent pair of side panels there is an integral web of material which may be viewed as comprising two separate portions separated by a crease line. Thus, between side panels 103 and 104 there is a web 109 comprising portions 109a and 109b separated by crease line 109'. Similarly, between side panels 105 and 106, there is a web 110 comprising portions 110a and 110b separated by crease line 110'. In a similar manner, panels 111 and 112 are formed.

The box shown in FIG. 7 is erected by folding the sides 103, 104, 105 and 106 upwards together about the crease lines shown. The webs 109, 110, 111 and 112 fold about their crease lines and, when the sides 103 to 106 are folded together, these webs are on the inside of the box. As can be seen from FIG. 7, in the erected box, two upstanding sides 114 and 115 are constituted by the side panels 104 and 105 respectively. The junction 116 between the two sides is formed where the crease lines 104' and 105' meet. In a similar fashion, the junctions between the panels 103 and 104, panels 103 and 106 and panels 106 and 105 are formed. The webs 109 to 112, in the folded box, provided a degree of structural integrity to the box but also, importantly, maintain a seal at the junction between the upstanding sides, for instance between sides 114 and 115 at the junction 116.

The top panels 107 and 108 are folded so as to lie parallel to the base 102 and overlying each other with the panel 108 uppermost. The top of the box is held down by the following arrangement. Provided at the outer ends of side panels 103 and 105 are flaps 117 which, although defined at their junction with the side panel partially by a crease line, also include a cut line between the flap 117 and the side panel 103 or 105. Thus, when the flap 117 is folded relative to the side panel 103 or 105, a slot is formed. Into this slot, may project downwardly an ear 118 which is provided on the top flap 118. Slots 119 in the lower flap 107 of the two top flaps 107 and 108 allow entry of the ears 118.

Finally, one of the side flaps 104 and the two top flaps 107 are provided with weakened regions shown by the broken and crossed lines 120 so that, once the box is erected, a weakened zone 121 is defined. The lines of weakness around the weakened zone 121 are such that separate hinges 122 and 123 are formed. This weakened zone 121 can by manually opened when the box is to be used for insertion of disposable articles. The weakened zone 121 is not removed completely, but is capable of being opened in two separate stages. Thus, the part of the weakened zone 121 in the top flap 108 can be broken so that the weakened area pivots about line 122. Alternatively, the whole of the weakened zone 121 may be forced downwards so that it pivots about line 123. The carton shown in FIG. 6 may be held together by gluing together chosen adjacent flaps.

Figure 9:
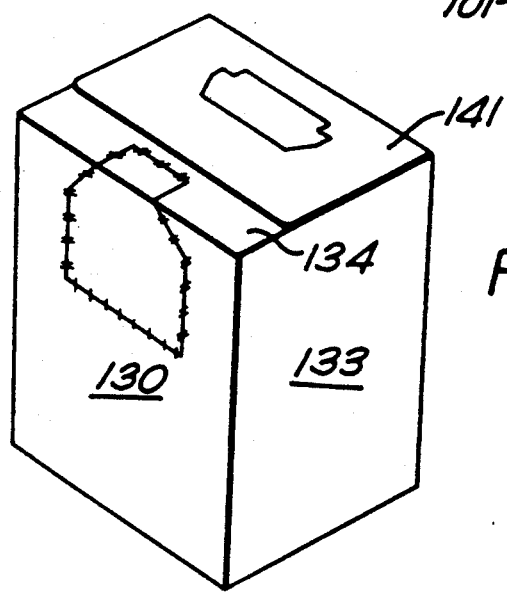
FIG. 9 shows the container erectable from the blank shown in FIG. 8.
Figure 8:
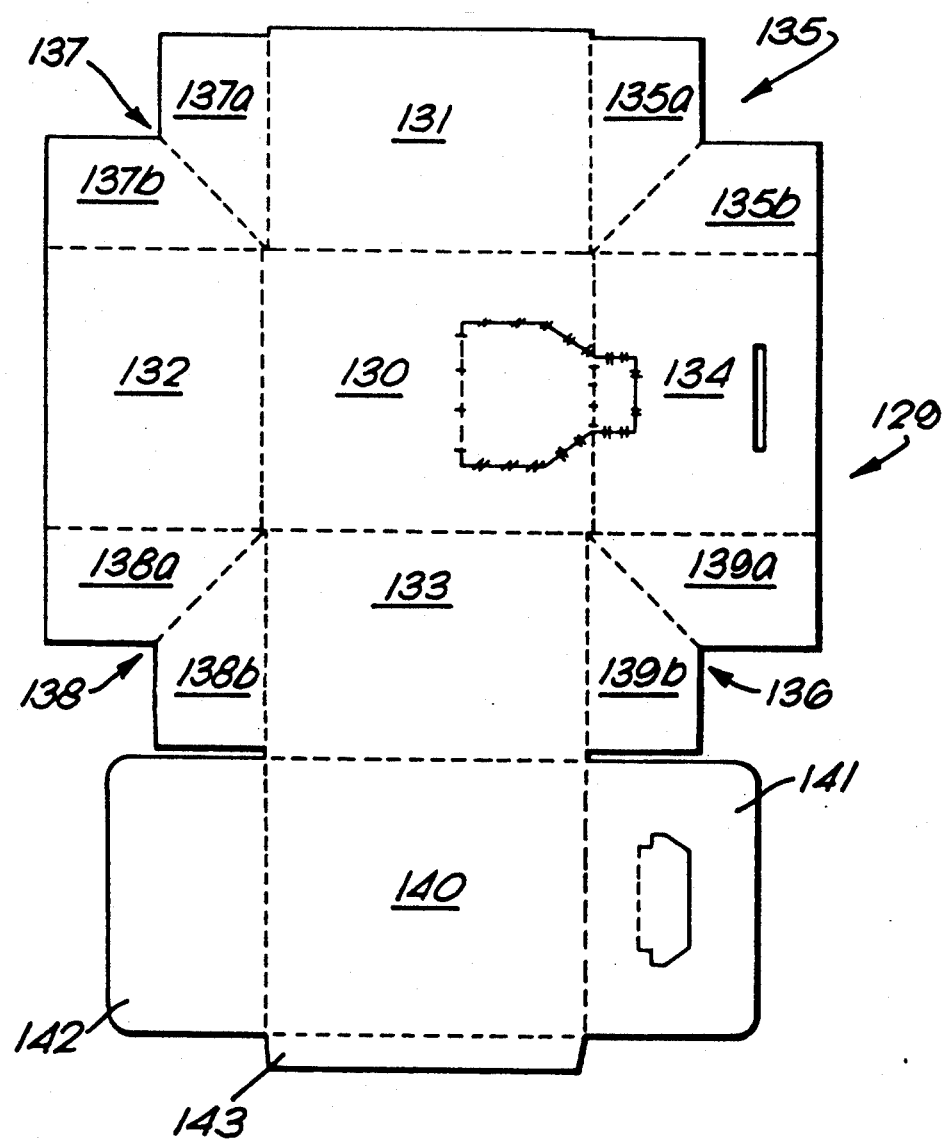
FIG. 8 shows a yet further form of blank.

Turning to FIGS. 8 and 9, the blank shown in FIG. 8 and the container (FIG. 9) into which the blank shown in FIG. 8 erects, are very similar to the blank and container shown in FIGS. 6 and 7 except that the erected carton shown in FIG. 9 is of a generally rectangular rather than truncated pyramidal shape. Thus FIG. 8 shows a blank 129 which comprises a central square panel 130 surrounded by side panels 131, 132, 133 and 134. Between the side panels are webs 135, 136, 137 and 138. The blank also includes a top panel 140 which has, projecting from each side, panels 141 and 142 and a small flap 143. Erection of the container involves folding the panels 131 to 134 about their crease lines with the panel 130, the webs being directed to the inside of the resultant container. The panel 140 is then caused to lay parallel and spaced from the panel 130 thereby enclosing the box, and the short flap 143 is glued to panel 131 to secure the box. Flap 142 may be glued to the inside of flap 132 whilst flap 141 is glued to the outside of flap 134 this giving the rectangular carton shown in FIG. 9. The weakened zone 143 in the carton is formed in like manner to that shown in FIGS. 6 and 7.

We claim:

1. A fold-up container for holding and incinerating disposable syringes comprising:

a base panel, a top panel and a plurality of side panels hingably connected to one another along a plurality of fold lines to define a closed container having an internal chamber dimensioned to receive one or more disposable syringes, an access opening into said chamber formed by a peripheral weakened line defining a tear strip, said weakened line located in at least one of said side panels and extending into a portion of said top panel, said carton formed of a corrugated paper-based fluting having an inner metal foil layer, defining said chamber, secured to one side of said fluting and an outer paper-based layer secured to an opposite side fluting, whereby said container resists puncturing by a syringe and maintains sufficient structural integrity to facilitate destruction of syringes by internal burning before the container itself is destroyed by burning.

2. A container as defined in claim 1 wherein said metal layer is an aluminum or ferric foil.

3. A container as defined in claim 1 wherein said blank includes a plurality of end panels wherein the sides of said container formed by said panels are several panels thick.

4. A container as defined in claim 1 wherein said blank comprises an integral arrangement of at least six panels separated by crease lines, including panels which represent, in the erected container, a top, a bottom and four sides, at least one of the panels being rectangular and having connected to each of its four sides one of the other panels, and between each pair of said other panels there being an integral web of material which in the erected container provides a seal between adjacent walls of the container.

* * * * *